United States Patent

Campbell et al.

(10) Patent No.: US 10,345,261 B2
(45) Date of Patent: Jul. 9, 2019

(54) DIFFERENTIAL MOBILITY SPECTROMETRY METHOD

(71) Applicant: DH Technologies Development PTE Ltd., Singapore (SG)

(72) Inventors: John Lawrence Campbell, Milton (CA); Yves Le Blanc, Newmarket (CA)

(73) Assignee: DH Technologies Development Pte. Ltd., Singapore (SG)

(*) Notice: Subject to any disclaimer, the term of this patent is extended or adjusted under 35 U.S.C. 154(b) by 0 days.

(21) Appl. No.: 15/540,770

(22) PCT Filed: Dec. 16, 2015

(86) PCT No.: PCT/IB2015/059698
§ 371 (c)(1),
(2) Date: Jun. 29, 2017

(87) PCT Pub. No.: WO2016/108126
PCT Pub. Date: Jul. 7, 2016

(65) Prior Publication Data
US 2018/0003675 A1 Jan. 4, 2018

Related U.S. Application Data

(60) Provisional application No. 62/098,700, filed on Dec. 31, 2014.

(51) Int. Cl.
*G01N 27/62* (2006.01)
*H01J 49/00* (2006.01)

(52) U.S. Cl.
CPC .......... *G01N 27/624* (2013.01); *H01J 49/004* (2013.01)

(58) Field of Classification Search
CPC ... G01N 27/622; G01N 27/624; H01J 49/004; H01J 49/26; H01J 49/34; H01J 49/36; H01J 49/40; H01J 49/0027; H01J 49/0031

See application file for complete search history.

(56) References Cited

U.S. PATENT DOCUMENTS 6,831,271 B1 * 12/2004 Guevremont .......... B01D 59/46
250/281
6,960,761 B2 * 11/2005 Clemmer ............. G01N 27/622
250/287

(Continued)

FOREIGN PATENT DOCUMENTS

WO  2008085351 A2  7/2008

OTHER PUBLICATIONS

International Search Report and Written Opinion for PCT/IB2015/059698 dated Apr. 25, 2015.

*Primary Examiner* — David E Smith

(57) ABSTRACT

Methods and systems are provided herein for varying the CoV about a nominal CoV-apex while monitoring the ion of interest corresponding to the nominal CoV-apex as it is transmitted by a DMS. In various aspects, the CoV can be swept or stepped across a series of values during the injection of ions into the DMS such that a composite spectra of the ion of interest transmitted by the DMS (or its product ions following one or more stages of fragmentation) can be generated so as to include the transmission of the particular ion at a CoV with optimum sensitivity (i.e., if distinct from the CoV-apex), thereby improving the robustness, accuracy, and/or selectivity during experimental conditions relative to known DMS techniques, which typically used a fixed CoV value for each ion of interest.

16 Claims, 4 Drawing Sheets

(56) References Cited

U.S. PATENT DOCUMENTS

| | | | | |
|---|---|---|---|---|
| 8,173,959 B1* | 5/2012 | Boumsellek | ......... | G01N 27/622 |
| | | | | 250/281 |
| 2004/0094704 A1* | 5/2004 | Miller | ................... | G01N 27/624 |
| | | | | 250/287 |
| 2005/0040330 A1* | 2/2005 | Kaufman | ............. | G01N 27/624 |
| | | | | 250/293 |
| 2005/0116160 A1 | 6/2005 | Guevremont | | |
| 2005/0253061 A1* | 11/2005 | Cameron | ............. | G01N 27/624 |
| | | | | 250/287 |
| 2006/0038121 A1* | 2/2006 | Guevremont | ........ | G01N 27/624 |
| | | | | 250/290 |
| 2008/0067350 A1 | 3/2008 | Li | | |
| 2009/0294650 A1 | 12/2009 | Schneider et al. | | |
| 2010/0230588 A1* | 9/2010 | Atkinson | ............ | G01N 27/624 |
| | | | | 250/283 |
| 2010/0282966 A1* | 11/2010 | Schneider | ............ | G01N 27/622 |
| | | | | 250/282 |
| 2010/0308216 A1* | 12/2010 | Clark | ................... | G01N 27/624 |
| | | | | 250/282 |
| 2011/0095175 A1* | 4/2011 | Bateman | .............. | G01N 27/624 |
| | | | | 250/282 |
| 2011/0183431 A1* | 7/2011 | Covey | ................. | G01N 27/624 |
| | | | | 436/173 |
| 2013/0084645 A1* | 4/2013 | Coon | ................... | G01N 33/483 |
| | | | | 436/173 |
| 2015/0074093 A1* | 3/2015 | Murthy | ................. | G01N 27/62 |
| | | | | 707/723 |

* cited by examiner

DIFFERENTIAL MOBILITY SPECTROMETRY METHOD

RELATED APPLICATIONS

This application claims the benefit of priority from U.S. Provisional Application Ser. No. 62/098,700 filed on Dec. 31, 2014, the entire content of which is incorporated by reference herein.

FIELD

The teachings herein relate to relate to mass spectrometry, and more particularly to methods and apparatus for differential mobility spectrometry.

BACKGROUND

A Differential Mobility Spectrometer (DMS), also referred to as a Field Asymmetric Waveform Ion Mobility Spectrometer (FAIMS) or Field Ion Spectrometer (FIS), typically performs gas-phase ion sample separation and analysis. In some circumstances, a DMS is interfaced with a mass spectrometer (MS) to take advantage of the atmospheric pressure, gas-phase, and continuous ion separation capabilities of the DMS and the detection accuracy of the MS. By interfacing a DMS with an MS, numerous areas of sample analysis, including proteomics, peptide/protein conformation, pharmacokinetics, and metabolism analysis have been enhanced. In addition to pharmaceutical and biotech applications, DMS-based analyzers have been used for trace level explosives detection and petroleum monitoring.

Differential mobility spectrometry is a variant of ion mobility spectrometry (IMS). A DMS, like an ion mobility spectrometer, is considered an ion mobility based analyzer because the DMS separates and analyzes ions based on the mobility characteristics of the ions. In an IMS, ions are pulsed into and pass through a drift tube while being subjected to a constant electric field. The ions interact with a drift gas in the drift tube and the interactions affect the time it takes for the sample ions to pass through the drift tube. The drift time and thus mobility is a function of the size, shape, and charge state of an ion and its interactions with the background gas. These interactions are specific for each analyte ion of a sample, leading to an ion separation based on more than just mass/charge ratio. In contrast, in a time-of-flight mass spectrometer (TOF-MS), there is a vacuum in the drift region of the MS and, therefore, an ion's time through the MS drift region is based on the ion's mass-to-charge ratio (m/z) in the collision-free environment of the vacuum.

A DMS is similar to an IMS in that the ions are separated in a drift gas, which is typically supplied from a gas source upstream of the DMS. However, unlike an IMS, the DMS uses an asymmetric electric field waveform that is applied between two parallel electrodes through which the ions pass, typically, in a continuous manner. RF voltages, often referred to as separation voltages (SV), are applied across the ion transport chamber, perpendicular to the direction of the transport gas flow. As a result of the SV, the ions' flight paths can deviate from the center of the chamber and migrate toward the walls unless their trajectory is corrected by a counterbalancing voltage, a DC potential often referred to as a compensation voltage (CoV) that is applied to electrodes to restore a stable trajectory for a particular ion caused by the difference between high field and low field ion mobilities. In some DMS systems, a modifier liquid can also be added to the drift gas to provide increased selectivity by clustering with ions to different degrees, thereby shifting these ions differential mobilities. In known devices, with the CoV of the DMS being set to a fixed value, ions can be continuously introduced into the DMS with only ion species with a particular differential mobility being transmitted by the DMS.

SUMMARY

Known techniques generally utilize a theoretical or empirical CoV value for a particular ion species under particular DMS conditions that are believed to maximize the transmission of the ion of interest so as to yield the highest sensitivity with the hope of minimizing interference from other background ions generated by the source (i.e., CoV-apex). However, any given ion will transmit through the DMS over a range of CoV values for a given SV, and this range of CoV depends, for example, on the residence time in the DMS, which can be controlled via the "resolution gas" (e.g., a throttle gas introduced to slow down ions). Though great care has been taken to ensure that SV-CoV values can be reproduced between systems, there exists a slight variability that can exist as a result of either minor differences in system tuning or from the source conditions used, for example. Accordingly, actual operating conditions of the DMS can vary from the theoretical conditions upon which the CoV-apex is determined such that the transmission of the ion of interest is not maximized. Thus, if one relies on database values of the CoV-apex under standard operating procedures of the DMS, quantitative applications (e.g., where multiple reaction monitoring or MRM is being used), the DMS may not be operating at optimum conditions. Likewise, in other workflows such as MRM-triggered enhanced product ion (EPI) data collection, the EPI could therefore be collected at less than optimum CoV values. Applicant has also found that the variability from the theoretical CoV can be particularly affected when resolution gas (with or without a modifier) is used in the DMS.

In accordance with various aspects of the present teachings, methods and systems are provided herein for varying the CoV applied to the DMS about the CoV-apex while monitoring the ion of interest transmitted by the DMS on a liquid-chromatography (LC) time scale (i.e., varying the CoV during different time points of the LC elution, with the concentration of the analyte of interest in the eluent being substantially constant between the time points). In various aspects, the CoV can be swept or stepped across a series of values during the injection of ions into the DMS such that a composite spectra of the ion of interest transmitted by the DMS (or its product ions following one or more stages of fragmentation) can be generated so as to include the transmission of the particular ion at a CoV with optimum sensitivity (i.e., if distinct from the CoV-apex), thereby improving the robustness, accuracy, and/or selectivity during experimental conditions relative to known DMS techniques. Moreover, it will be appreciated in light of the present teachings that the CoV-apex can be adapted to gain maximum selectivity based on the results of the methods described herein. By way of example, in an adaptive CoV technique in accordance with the present teachings, it may be found that the optimum conditions from a selectivity perspective may reside at a CoV that is on the boundary of the range of CoVs applied while collecting data from matrix samples such that the CoV-apex can be adapted (e.g., re-calibrated) following data collection (post-acquisition). By way of example, the present teachings can be implemented in an LC-IDA workflow (e.g., MRM-triggered EPI), with any improvements in the data, library searching, etc., being observed so as to improve future analyses. Similarly, the teachings herein can be applied to permit analysis when the optimal CoV value is unknown or if there is drift of the optimum CoV value during the analysis of a sample.

In accordance with various aspects of the present teachings, a method of operating a system comprising a DMS is provided, the method comprising injecting a stream of ions into a DMS during a first duration, the stream of ions containing or suspected of containing an ion species of interest; determining a compensation voltage apex (CoV-apex) for the ion species of interest in the DMS; varying the CoV-apex applied to the DMS over a range about the determined CoV-apex during the first duration; and detecting the ion species of interest transmitted by the DMS during the first duration. In some aspects, the ions can be transmitted through the differential mobility spectrometer in a drift gas with or without a modifier liquid.

In various aspects, the CoV-apex represents a nominal optimum for transmission of the ion species of interest based on operating conditions of the DMS, though the CoV-apex can be determined in a variety of manners. In some aspects, for example, the CoV-apex can be provided by a look-up table. For example, the CoV-apex for the ion species of interest can be determined based on a theoretical optimum transmission compensation voltage. In some aspects, the CoV-apex and/or the range about the CoV-apex can be selected by a user. In various aspects, the range can be determined through a user-selected deviation from the CoV-apex.

The range of CoV values applied to the DMS can be determined in a variety of manners. For example, the range about the CoV-apex can be predetermined. By way of example, the range can represent ±1.0V of the CoV-apex, and the CoV can be varied in stepwise increments of 0.1V. In various aspects, the range about the CoV-apex comprises a range between a first CoV value less than the CoV-apex and a second CoV value greater than the CoV-apex. In some aspects, the CoV applied to the DMS can be discretely varied, in stepwise fashion, between the first CoV value and the second CoV value (e.g., from low to high or vice versa). Alternatively, the CoV can be continuously varied (e.g., swept) between the first CoV value and the second CoV value (e.g., from low to high or vice versa).

In accordance with various aspects, detecting the ion of interest can comprise generating a mass spectra of ions transmitted by the DMS during the first duration. The ion of interest can be detected directly, or in some aspects, detecting the ion of interest can comprise monitoring one or more products of fragmentation of the ions transmitted by the DMS during the first duration. By way of example, the method can include fragmenting the ions transmitted by the DMS and the fragments can be detected. In various aspects, the m/z for the detected fragments can be calculated and a mass spectrum corresponding to the ion fragment m/z data can be generated.

In various aspects, the method further comprises applying a fixed separation voltage (SV) RF signal to the DMS while varying the CoV about the determined CoV-apex. In some aspects, the separation voltage RF signal represents a nominal optimum SV based on operating conditions of the DMS, though the SV can be determined in a variety of manners. In some aspects, for example, the SV can be provided by a look-up table (e.g., based on theoretical or empirical data), or can be selected by a user.

In accordance with various aspects of the present teachings, an apparatus for analyzing ions is provided, the apparatus comprising an ion source configured to generate ions from a sample containing or suspected of containing an ion species of interest; a DMS configured to receive the plurality of ions from the ion source and transmit one or more ions species based on the differential mobility of the ion species therein; and a detector for detecting the ion species transmitted by the DMS. A controller can be operatively coupled to the ion source, the DMS, and the detector, and configured to cause the ion source to inject a stream of ions into the DMS during a first duration; determine a CoV-apex for the ion species of interest in the DMS; vary the CoV applied to the DMS over a range about the determined CoV-apex during said first duration; and detect the ion species of interest transmitted by the DMS during said first duration. In various aspects, the apparatus can further include data storage associated with the controller configured to store the CoV-apex for one or more ion species under operating conditions of the DMS. In some aspects, the apparatus can comprise a drift gas supply for providing a drift gas for flowing through the DMS and a modifier liquid supply for supplying a modifier liquid to the drift gas.

In various aspects, the range about the CoV-apex can comprise a range between a first CoV value less than said CoV-apex and a second CoV value greater than said CoV-apex. The controller can be configured to discretely vary (in stepwise fashion) or continuously vary (e.g., sweep) the CoV applied to the DMS between the first CoV value and the second CoV value. The range can represent a predetermined range about the CoV-apex, for example, ±1.0V of the CoV-apex, and the CoV can be varied continuously or in stepwise increments of 0.1V.

In various aspects, the apparatus can further comprise an input device that is configured to receive an input from a user regarding the CoV-apex and/or the range about said CoV-apex. In some aspects, for example, the range can be determined through a user-selected deviation from the CoV-apex.

In some aspects, the apparatus can also include a fragmentor disposed between the differential mobility spectrometer and the detector, and configured to fragment the ions transmitted by the DMS, with the detector being configured to detect the ion species of interest by detecting one or more fragments of the ion species of interest. For example, the fragmentor can be a collision cell (e.g., Q2) where ions are fragmented as they transit the fragmentor (e.g., beam-type fragmentation) or via specific resonant excitation after a short trapping period in the fragmentor. In various aspects, the controller can be configured to calculate the m/z for each fragment detected by the detector and/or generate a mass spectrum corresponding to the ion fragment m/z data during the first duration.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

In various aspects, methods and systems are provided herein for varying the CoV about the CoV-apex while monitoring the ion of interest corresponding to the nominal CoV-apex as it is transmitted by the DMS. In various aspects, the CoV can be swept or stepped across a series of values during the injection of ions into the DMS such that a composite spectra of the ion of interest transmitted by the DMS (or its product ions following one or more stages of fragmentation) can be generated so as to include the transmission of the particular ion at a CoV with optimum sensitivity (i.e., if distinct from the CoV-apex), thereby improving the robustness, accuracy, and/or selectivity during experimental conditions relative to known DMS techniques.

Figure 1:
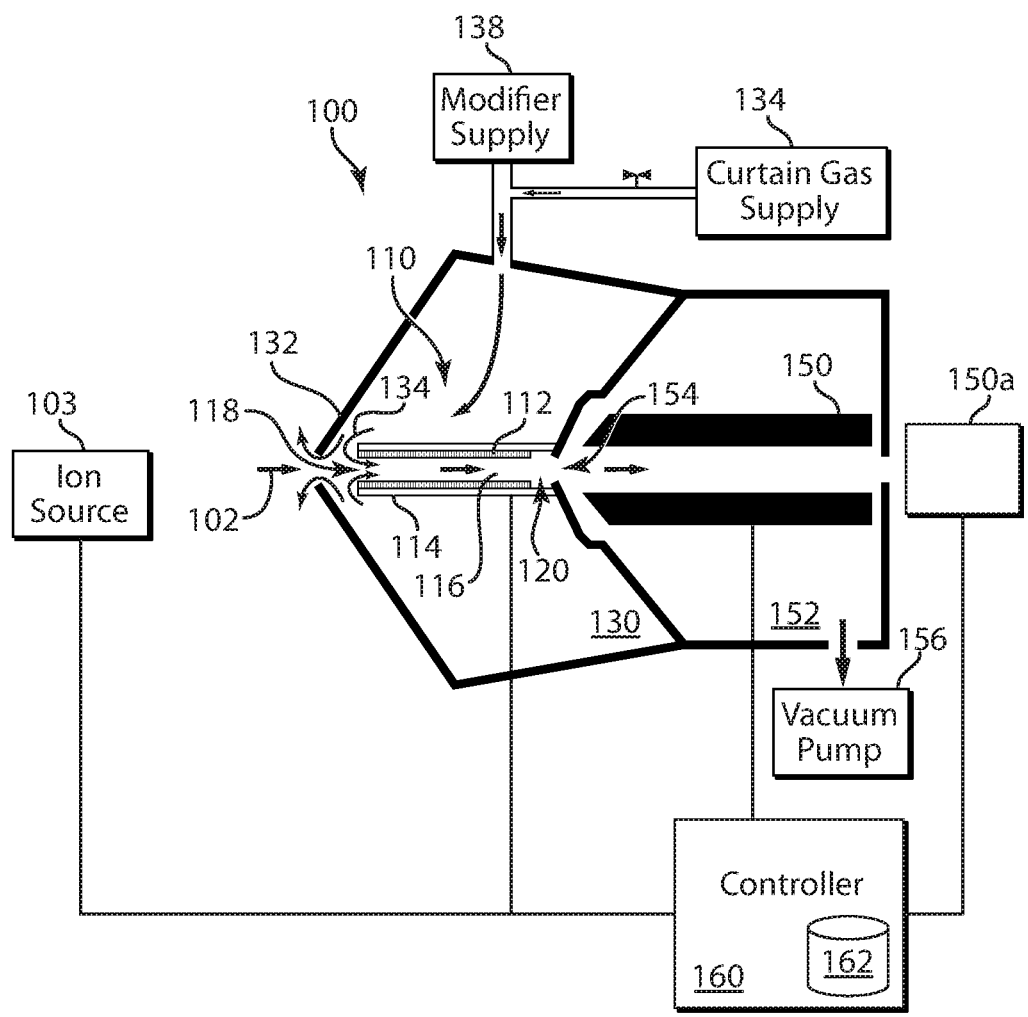
FIG. 1, in a schematic diagram, illustrates an exemplary differential mobility spectrometer/mass spectrometer system in accordance with an aspect of various embodiments of the applicant's teachings.

With reference now to FIG. 1, an exemplary differential mobility spectrometer/mass spectrometer system 100 in accordance with various aspects of applicant's teachings is illustrated schematically. As shown in FIG. 1, the differential mobility spectrometer/mass spectrometer system 100 generally comprises an ion source 103, a differential mobility spectrometer (DMS) 110, a first vacuum lens element 150 of a mass spectrometer (hereinafter generally designated mass spectrometer 150) in fluid communication with the DMS 110, and a controller 160 operatively coupled to the ion source 103, the DMS 110, and the mass spectrometer 150 for controlling operation of the system 100 as discussed otherwise herein.

In the exemplary embodiment depicted in FIG. 1, the differential mobility spectrometer 110 comprises a pair of opposed electrode plates 112 surrounded by an electrical insulator 114 that supports the electrode plates 112 and insulates them from other conductive elements. The electrode plates 112 surround a drift gas 116 that drifts from an inlet 118 of the differential mobility spectrometer 110 to an outlet 120 of the differential mobility spectrometer 110. The outlet 120 of the differential mobility spectrometer 110 releases the drift gas 116 into an inlet 154 of a vacuum chamber 152 containing the mass spectrometer 150. As will be appreciated by a person skilled in the art, the differential mobility spectrometer/mass spectrometer system 100 represents only one possible configuration for use in accordance with various aspects of the systems, devices, and methods described herein. By way of non-limiting example, the differential mobility spectrometer can be a differential mobility spectrometer, or FAIMS devices of various geometries such as parallel plate, curved electrode, or cylindrical FAIMS device, among others.

The differential mobility spectrometer 110 can be contained within a curtain chamber 130 that is defined by a curtain plate or boundary member 132 and is supplied with a curtain gas from a curtain gas supply 134. The pressure of the curtain gases in the curtain chamber 130 can be maintained at or near atmospheric pressure (i.e., 760 Torr). It will be appreciated by a person skilled in the art that the curtain gas supply 134 can provide any pure or mixed composition curtain gas to the curtain gas chamber via curtain gas conduits at flow rates determined by a flow controller and valves, for example. By way of non-limiting example, the curtain gas can be air, $O_2$, He, $N_2$, $CO_2$, or any combination thereof. As shown in FIG. 1, the system 100 can also include a modifier supply 138 for supplying a modifier to the curtain gas. As noted above, the modifier agents can be added to the curtain gas to cluster with ions differentially during the high and low field portions of the SV. As will be appreciated by a person skilled in the art, the modifier supply can be a reservoir of a solid, liquid, or gas through which the curtain gas is delivered to the curtain chamber 130. By way of example, the curtain gas can be bubbled through a liquid modifier supply. Alternatively, a modifier liquid or gas can be metered into the curtain gas, for example, through an LC pump, syringe pump, or other dispensing device for dispensing the modifier into the curtain gas at a known rate. For example, the modifier can be introduced using a pump so as to provide a selected concentration of the modifier in the curtain gas. The modifier supply 138 can provide any modifier including, by way of non-limiting example, acetone, water, methanol, isopropanol, methylene chloride, methylene bromide, or any combination thereof. Optionally, the curtain gas conduit and/or curtain chamber 130 can include a heater for heating the mixture of the curtain gas and the modifier to further control the proportion of modifier in the curtain gas.

As will be appreciated by a person skilled in the art, the differential mobility spectrometer/mass spectrometer system 100 can additionally include one or more additional mass analyzer elements 150a downstream from vacuum chamber 152. By way of example, ions can be transported through vacuum chamber 152 and through one or more additional differentially pumped vacuum stages containing one or more mass analyzer elements 150a. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell (Q2) located between them. In some aspects, for example, the collision cell (Q2) can be operated as a fragmentor for fragmenting the ions transmitted by the differential mobility spectrometer 110, with the detector being configured to detect the ion species of interest by detecting one or more fragments of the ion species of interest. It will be apparent to those skilled in the art that there may be a number of other ion optical elements in the system. Other type of mass analyzer such as single quadrupole, ion trap (3D or 2D), hybrid analyzer (quadrupole-time of flight, quadrupole-linear ion trap, quadrupole-orbitrap), orbitrap or time-of-flight mass spectrometer, could also be used.

Ions 102 can be provided from an ion source 103 and emitted into the curtain chamber 130 via curtain chamber inlet 134. As will be appreciated by a person skilled in the art, the ion source can be virtually any ion source known in the art, including for example, a continuous ion source, a pulsed ion source, an atmospheric pressure chemical ionization (APCI) source, an electrospray ionization (ESI) source, an inductively coupled plasma (ICP) ion source, a matrix-assisted laser desorption/ionization (MALDI) ion source, a glow discharge ion source, an electron impact ion source, a chemical ionization source, or a photoionization ion source, among others. The pressure of the curtain gases in the curtain chamber 130 (e.g., ~760 Torr) can provide both a curtain gas outflow out of curtain gas chamber inlet 134, as well as a curtain gas inflow into the differential mobility spectrometer 110, which inflow becomes the drift gas 116 that carries the ions 102 through the differential mobility spectrometer 110 and into the mass spectrometer 150 contained within the vacuum chamber 152, which can be maintained at a much lower pressure than the curtain chamber 130. For example, the vacuum chamber 152 can be maintained at a pressure of 2.3 Torr by a vacuum pump 156. As the curtain gas within the curtain chamber 130 can include a modifier, the drift gas 116 can also comprise a modifier.

As discussed otherwise herein, the electrode plates 112 can be coupled to a power source (not shown) such that an RF voltage (i.e., a separation voltage (SV)) can be applied to the electrode plates 112 to generate an electric force in a direction perpendicular to that of the drift gas flow 116. As a result, ions contained within the drift gas tend to migrate radially away from the axis of the drift tube by a characteristic amount during each cycle of the RF waveform due to differences in mobility during the high field and low field portions. A DC potential (i.e., a compensation voltage (CoV)), is applied to the electrode plates 112 to provide a counterbalancing electrostatic force to that of the SV. The CoV can be tuned so as to preferentially restore a stable trajectory to particular ions such that they will be sampled by the mass spectrometer 150 via its inlet 154. Depending on the application, the CoV can be set to a fixed value such that only ion species exhibiting a particular differential mobility are transmitted through the outlet 120 of the differential mobility spectrometer 110 (the remaining species of ions drift toward the electrodes 112 and are neutralized thereby). As will be appreciated by a person skilled in the art, the differential mobility spectrometer 110 can also operate in "transparent" mode, for example, by setting SV to zero such that substantially all ions are transmitted therethrough without experiencing a net radial force.

As noted above, the exemplary system 100 can additionally comprise a controller 160 for controlling operation thereof. By way of example, the controller 160 can include a processor for processing information. Controller 160 also includes data storage 162 for storing mass spectra, CoV-apex data (e.g., in a database or library), and instructions to be executed by processor, etc. Data storage 162 also may be used for storing temporary variables or other intermediate information during execution of instructions to be executed by the processor.

The controller 160 can also be operatively associated with an output device such as a display (e.g., a cathode ray tube (CRT) or liquid crystal display (LCD), for displaying information to a computer user) and/or an input device including alphanumeric and other keys and/or cursor control, for communicating information and command selections to the processor. Consistent with certain implementations of the present teachings, the controller 160 can execute one or more sequences of one or more instructions contained in data storage 162, for example, or read into memory from another computer-readable medium, such as a storage device (e.g., a disk). Implementations of the present teachings are not limited to any specific combination of hardware circuitry and software.

Figure 2:
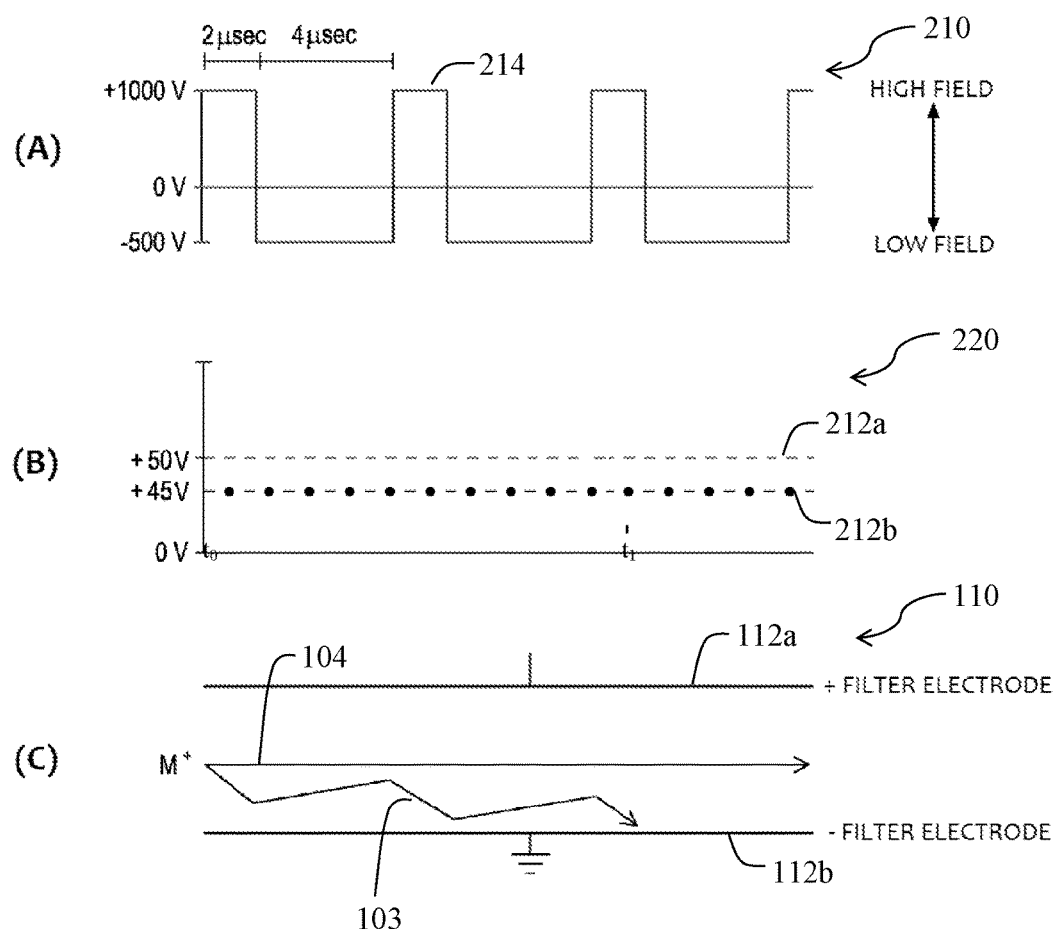
FIG. 2A depicts an exemplary timing diagram for generating an asymmetric electric field in DMS of FIG. 1.
FIG. 2B depicts an exemplary timing diagram for operating the filter electrodes using a fixed CoV in the DMS of FIG. 1.
FIG. 2C, in schematic diagram, depicts exemplary paths for groups of ions within the DMS filter subjected to the combined electric fields of FIGS. 2A and 2B.
Figure 3:
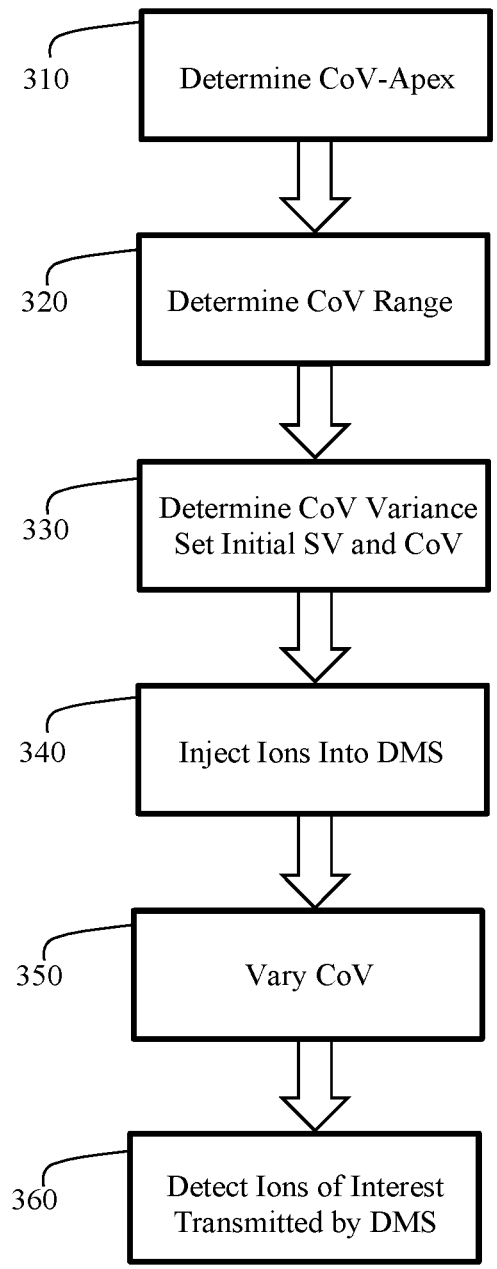
FIG. 3 is a flowchart showing an exemplary method for analyzing an ion of interest in the system of FIG. 1 in accordance with various aspects of the present teachings.

With reference now to FIGS. 2A-C, the exemplary DMS 110 separates the ions in a drift gas based on their mobility when subject to an asymmetric electric field generated between the parallel electrodes 112 through which the ions pass, typically, in a continuous manner. In DMS, the electric field waveform typically has a high field duration at one polarity and then a low field duration at an opposite polarity. The duration of the high field and low field portions can be applied such that the net force being applied to ions across the DMS filter electrodes is zero. Such an electric field can be generated, for example, through the application of RF voltages, often referred to as separation voltages (SV), across the drift tube in a direction perpendicular to that of a drift gas flow. Ions of a given species tend to migrate radially away from the axis of the transport chamber by a characteristic amount during each cycle of the RF waveform due to differences in mobility during the high field and low field portions. With specific reference to FIG. 2A, a plot 210 of an exemplary, time-varying, RF, and/or asymmetric high and low voltage waveform 214 that can be applied to generate an asymmetric electric field is depicted. Although the waveform of FIG. 2A is depicted as a square-wave function with a total period of 6 μsec, it will be apparent to those of skill in the relevant arts that other waveform shapes and periods are possible, including waveforms constructed by summation of two sine waves, by way of non-limiting example.

In DMS, a DC potential is also applied to the electrodes 112a,b, with the difference in DC potential between the electrodes commonly referred to as a compensation voltage (CoV) that generates a counteracting electrostatic force to that of the SV. Typically, as noted above, the CoV can be set to a fixed value to pass only an ion species with a particular differential mobility while the remaining species of ions drift toward the electrodes 112a,b and are neutralized thereat, as shown in FIG. 2B. The plot 220, for example, depicts exemplary DC offset voltages 212a,b that are applied to filter electrodes 112a,b, respectively, such that the CoV is fixed at the CoV-apex (e.g., +5V (i.e., 50V–45V) in this example).

With reference now to FIG. 2C, the combined effect of the electric fields generated by the waveforms in FIGS. 2A and 2B is shown in schematic representation for two species of ions. For the first species, the ion's mobility in the asymmetric electric field indicates a net movement 103 towards the bottom electrode 112b of the DMS 110 upon injection. (It should be appreciated in view of the depicted motion of the first species that, in a DMS, the ion's mobility is not constant under the influence of the low electric field compared to the high electric field.) However, for the second ion species, the +5V CoV applied to the filter electrodes 112a,b maintains the second ion species along a safe trajectory 104 for the ion through the DMS 110 (i.e., without striking one of the filter electrodes 112a,b) to allow, for example, detection by the detector 150 of FIG. 1. It is noted that trajectory 104 is shown schematically as being averaged over a full cycle of the waveform, and thus does not show the ion oscillations for each high and low portion of the waveform.

With reference now to FIGS. 3 and 4A-C, exemplary methods of operating the differential mobility spectrometer/mass spectrometer system 100 of FIG. 1. As shown at step 310 of the flow diagram of FIG. 3, the method can comprise determining the CoV-apex to be applied to the DMS 110. As will be appreciated by a person skilled in the art, the CoV-apex (e.g., +5V as shown in FIG. 2B) can be determined based on theoretical or empirical information based on the standard operating conditions of the DMS 110, with reference for example, to the SV to be applied to the DMS 110, the mobility of the ion of interest, the drift gas identity and flow rate, and the modifier. By way of example, the CoV-apex can be input by a user or determined automatically (e.g., using the controller 160). By way of example, after setting up the remainder of the operating parameters (e.g., SV), the controller 160 can access a library (e.g., data storage 162) of CoV-apex under the selected operating parameters. For example, as shown in the trace 401 of FIG. 4A, the library can contain data regarding the relative intensity of the ion of interest at various CoV values such that the CoV 402 corresponding to the maximum intensity of the transmitted ions representing the CoV-apex can be determined. Alternatively, it will be appreciated that the user can select a CoV-apex based on empirical data or experience, for example, of the user's particular system 100. In some aspects, the applied SV (e.g., an optimum SV) can be determined by the user or automatically by the controller 160, for example, by referencing a table or library of standard DMS operating parameters (e.g., based on theoretical or empirical data).

Figure 4A:
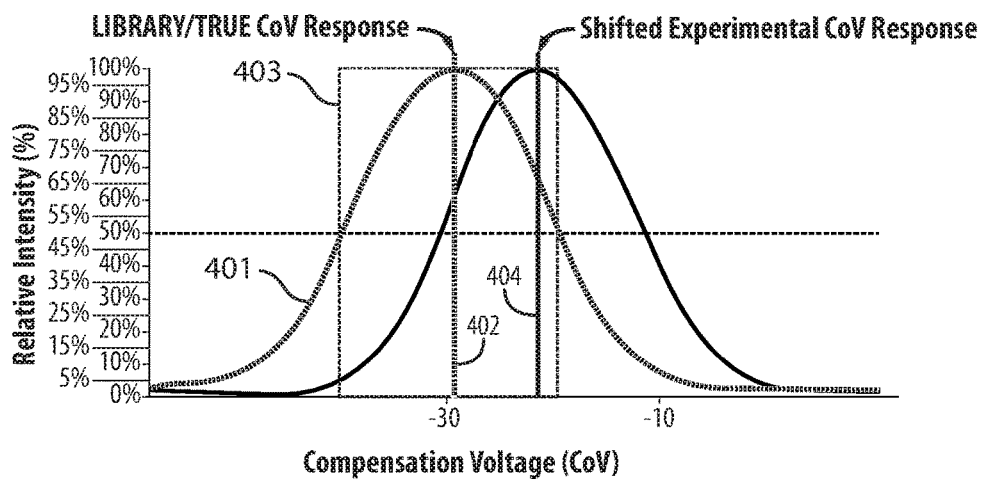
FIG. 4A depicts exemplary data regarding the relative intensity of the ion of interest at various CoV values utilized in determining the CoV-apex in accordance with various aspects of the present teachings.

As shown at step 320, a range of the CoV about the CoV-apex can then be determined, again via user input or the controller 160. By way of example, a voltage difference between the lowest CoV value and the highest CoV value to be applied to the electrodes 112a,b can be specified by the user (e.g., within ±1V of the CoV-apex), by specifying the lower and upper bounds of the range (e.g., the CoV-apex can be one of these bounds), or by specifying a deviation from the CoV-apex (e.g., by % of CoV, by number of standard deviations). Alternatively, in some aspects, the range can be pre-determined by the system 100, for example, such that only the CoV-apex need be determined in step 310, with the range being determined automatically by the controller in step 320. As shown in FIG. 4A, for example, upon determining the CoV-apex 402 in step 310, the range of the CoV can be selected to correspond to the full-width at half-maximum (FWHM) of theoretical or historical data of the relative intensity of the transmitted ion, as shown by the dotted box 403 of FIG. 4A.

Figure 4B:
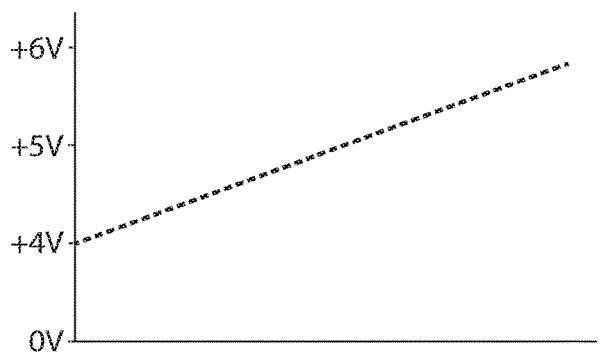
FIG. 4B depicts one exemplary continuous technique for varying the CoV in method of FIG. 3 in accordance with various aspects of the present teachings.
Figure 4C:
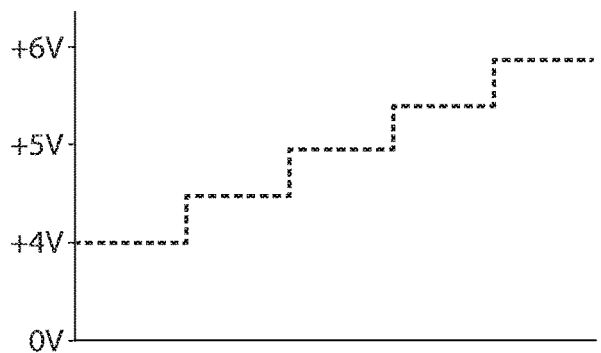
FIG. 4C depicts one exemplary stepwise technique for varying the CoV in method of FIG. 3 in accordance with various aspects of the present teachings.

As shown in step 330, it can then be determined the manner in which the CoV applied to the electrodes will be varied across the range determined in step 320. For example, as shown in FIG. 4, the range of CoV determined in step 320 can be applied such that the CoV varies continuously (e.g., continuously increases as shown in FIG. 4B) or varies in a stepwise manner (as shown in FIG. 4C). By way of example, if the electrodes 112a,b are configured to have a stepwise CoV applied thereto, the number of increments in the range, the duration of increments, and/or the size of the increments can be pre-determined or selected (e.g., via user input or by the controller 160).

Upon setting these parameters and applying an initial SV and CoV to the electrodes 112a,b as determined in step 330, the ion source can be activated such that a stream of ions containing or suspected of containing the ion species of interest (i.e., the ion corresponding to the determined CoV-apex) can be continuously injected into the DMS 110 in step 340. As the ions generated by the ion source traverse the filter electrodes, the SV and CoV in combination will tend to neutralize extraneous ions while transmitting the ion of interest from the downstream end of the DMS 110 to the mass spectrometer 150, for example.

In step 350, as the sample ions continue to be injected (e.g., for a duration corresponding to a substantially constant ion concentration in an eluent), the CoV can be varied in accordance with the function determined in step 330. By way of example, if the CoV is to be varied continuously, the initial CoV (e.g., +4V) applied to the electrodes 112a,b can be linearly increased to the CoV value at the upper end of the range (e.g., +6V) over the selected duration, as shown in FIG. 4B. Alternatively, as shown in FIG. 4C, if the CoV is to be varied in a stepwise manner, the initial CoV (e.g., +4V) applied to the electrodes 112a,b can be increased incrementally to the CoV value at the upper end of the range (e.g., +6V) over the selected duration. Though four stepwise increments of +0.5V are depicted in FIG. 4C, it will be appreciated in light of the present teachings that any number and size of CoV increments can be applied to the electrodes during the duration to vary the CoV about the CoV-apex. By way of example, the system 100 default to adjust the CoV by 0.1V in each increment.

In step 360, the ions that pass through the DMS 110 can be transmitted to the detector (e.g., to detect the ion species of interest directly) or can be subject to one or more additional analysis steps. By way of example, the ions transmitted by the DMS 110 can be subject to fragmentation with the m/z transitions between the precursor ions and product ions (i.e., fragment ions) being monitored to confirm the identity of and/or quantify the ion of interest in the sample. In an MRM-triggered EPI mode, the ions transmitted by the DMS 110 can be transmitted to a fragmentor (e.g., Q2), fragmented therein, and if the detected MRM transitions meet threshold criteria, trigger the generation of additional MS/MS steps such that the fragments can be collected in another mass analyzer (e.g., Q3) and analyzed. In each aspect discussed above, the detector 150a can be configured to detect the ions transmitted thereto, such that the controller 160 can calculate the m/z of the ions and/or generate a composite mass spectra of the ion of interest (or a product ion mass spectra) acquired during the duration of the varying CoV in accordance with the present teachings.

It will be appreciated in light of the present teachings that the CoV-apex can be adapted to obtain maximum selectivity based on the results of the methods described herein. By way of example, in an adaptive CoV technique in accordance with the present teachings, it may be found that the optimum conditions may reside at a CoV that is on the boundary (or outside the boundary) of the experimental range of CoVs applied while collecting data from matrix samples such that the CoV-apex can be adapted (e.g., re-calibrated) following data collection (post-acquisition). By way of example, with reference again to FIG. 4A, based on the data obtained from utilizing the theoretical or nominal CoV-apex 401 and window 403, it may be determined that under experimental conditions, the actual CoV-apex 404, has shifted to a higher value (to the right). Accordingly, in some aspects, the processor 160 can adapt such that under similar experimental condition in a subsequent run, for example, the CoV apex can be revised to increase sensitivity.

It should be appreciated that numerous changes can be made to the disclosed embodiments without departing from the scope of the present teachings. While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

The invention claimed is:

1. A method of operating a system comprising a differential mobility spectrometer, the method comprising:
   (a) injecting a stream of ions into a differential mobility spectrometer during a first duration, the stream of ions containing or suspected of containing an ion species of interest;
   (b) determining a compensation voltage apex for the ion species of interest in the differential mobility spectrometer, wherein the compensation voltage apex represents a nominal optimum for transmission of the ion species of interest based on operating conditions of the differential mobility spectrometer that are provided by a look-up table or wherein the compensation voltage apex for the ion species of interest is determined based on a theoretical optimum transmission compensation voltage;
   (c) varying the compensation voltage applied to the differential mobility spectrometer over a predetermined range about the determined compensation voltage apex during said first duration;
   (d) detecting the ion species of interest transmitted by the differential mobility spectrometer during said first duration and generating a composite spectra of the ion species of interest.

2. The method of claim 1, wherein said range about the compensation voltage apex comprises a range between a first compensation voltage value less than said compensation voltage apex and a second compensation voltage value greater than said compensation voltage apex, and wherein the range represents ±1.0V.

3. An apparatus for analyzing ions comprising:
   an ion source configured to generate ions from a sample containing or suspected of containing an ion species of interest;
   a differential mobility spectrometer configured to receive the plurality of ions from the ion source and transmit one or more ions species based on the differential mobility of the ion species therein;
   a detector for detecting the ion species transmitted by the differential mobility spectrometer; and
   a controller operatively coupled to the ion source, the differential mobility spectrometer, and the detector, and configured to:
      cause the ion source to inject a stream of ions into the differential mobility spectrometer during a first duration;
      determine a compensation voltage apex for the ion species of interest in the differential mobility spectrometer, wherein the compensation voltage apex represents a nominal optimum for transmission of the ion species of interest based on operating conditions of the differential mobility spectrometer that are provided by a look-up table or wherein the compensation voltage apex for the ion species of interest is determined based on a theoretical optimum transmission compensation voltage;
      vary the compensation voltage applied to the differential mobility spectrometer over a predetermined range about the determined compensation voltage apex during said first duration; and
      detect the ion species of interest transmitted by the differential mobility spectrometer during said first duration and generating a composite spectra of the ion species of interest.

4. The apparatus of claim 3, further comprising data storage associated with the controller, wherein the data storage is configured to store compensation voltage apex for one or more ion species under operating conditions of the differential mobility spectrometer.

5. The apparatus of claim 3, wherein said range about the compensation voltage apex comprises a range between a first compensation voltage value less than said compensation voltage apex and a second compensation voltage value greater than said compensation voltage apex.

6. The apparatus of claim 5, wherein the controller is configured to discretely vary, in stepwise fashion, the compensation voltage applied to the differential mobility spectrometer between the first compensation value and the second compensation value.

7. The apparatus of claim 5, wherein the controller is configured to continuously vary the compensation voltage applied to the differential mobility spectrometer between the first compensation value and the second compensation value.

8. The apparatus of claim 3, wherein said represents ±1.0V of the compensation voltage apex.

9. The apparatus of claim 3, wherein said range is determined through a user-selected deviation from the compensation voltage apex.

10. The apparatus of claims 3, further comprising a fragments disposed between the differential mobility spectrometer and the detector, wherein the fragmentor is configured to fragment the ions transmitted by the differential mobility spectrometer, and wherein the detector is configured to detect the ion species of interest by detecting one or more fragments of the ion species of interest.

11. The apparatus of claim 9, wherein the controller is configured to calculate the m/z for each fragment detected by the detector.

12. The apparatus of claim 10, wherein the fragmentor comprises a collision cell wherein beam-type fragmentation is implemented.

13. The apparatus of claim 10, wherein the fragmentor comprises a collision cell wherein resonance excitation for fragmentation is implemented.

14. The apparatus of claim 3, further comprising a drift gas supply for providing a drift gas for flowing through the differential mobility spectrometer and a modifier liquid supply for supplying a modifier liquid to the drift gas.

15. The apparatus of claim 8, wherein the compensation voltage is varied in stepwise increments of 0.1V.

16. The apparatus of claim 11, wherein the controller is configured to generate a mass spectrum corresponding to the ion fragment m/z data during said first duration.

* * * * *